(12) United States Patent
Gilday et al.

(10) Patent No.: US 7,705,145 B2
(45) Date of Patent: Apr. 27, 2010

(54) PROCESS FOR THE PREPARATION OF 4-(3'-CHLORO-4'-FLUOROANILINO)-7-METHOXY-6-(3-MORPHOLINOPROPOXY)QUINAZOLINE

(75) Inventors: John Peter Gilday, Bristol (GB); David Moody, Manchester (GB)

(73) Assignee: AstraZeneca AB, Sodertalje (SE)

( * ) Notice: Subject to any disclaimer, the term of this patent is extended or adjusted under 35 U.S.C. 154(b) by 842 days.

(21) Appl. No.: 10/527,461

(22) PCT Filed: Sep. 9, 2003

(86) PCT No.: PCT/GB03/03923

§ 371 (c)(1), (2), (4) Date: Mar. 11, 2005

(87) PCT Pub. No.: WO2004/024703

PCT Pub. Date: Mar. 25, 2004

(65) Prior Publication Data

US 2006/0003999 A1 Jan. 5, 2006

(30) Foreign Application Priority Data

Sep. 13, 2002 (GB) ................................ 0221245.4

(51) Int. Cl.
C07D 413/12 (2006.01)
(52) U.S. Cl. ..................................................... 544/116
(58) Field of Classification Search .................. 544/116
See application file for complete search history.

(56) References Cited

U.S. PATENT DOCUMENTS

| 5,457,105 | A | 10/1995 | Barker |
| 5,616,582 | A | 4/1997 | Barker |
| 5,770,599 | A | 6/1998 | Gibson |
| 6,294,532 | B1 | 9/2001 | Thomas et al. |
| 6,806,274 | B1 | 10/2004 | Crawley et al. |
| 2003/0187002 | A1 | 10/2003 | Mortlock et al. |

FOREIGN PATENT DOCUMENTS

| EP | 0 566 226 A | 10/1993 |
| EP | 0566226 | 10/1993 |
| EP | 1466907 | 10/2004 |
| EP | 1481971 | 12/2004 |
| JP | 11228515 | 8/1999 |
| JP | 11292855 | 10/1999 |
| WO | 96/33980 A | 10/1996 |
| WO | WO 96/33980 | 10/1996 |
| WO | 99/10349 A | 3/1999 |
| WO | WO 99/10349 | 3/1999 |
| WO | 01/04102 A | 1/2001 |
| WO | WO 01/04102 | 1/2001 |
| WO | 02/00649 A | 1/2002 |
| WO | WO 02/00649 | 1/2002 |
| WO | WO 02/48089 | 6/2002 |
| WO | WO 03/051849 | 6/2003 |
| WO | WO 03/064377 | 8/2003 |
| WO | WO 03/066602 | 8/2003 |

OTHER PUBLICATIONS

Database CAS Online on STN, Chem. Abstr., Accession No. 1908:15495, Oddo, Bernardo, Gazzetta Chimica Italiana (1908), 37(2), 356-66, abstract only.*
Database CAS Online on STN, Chem. Abstr., Accession No. 1945:19058, Adams et al., Journal of the American Chemical Society (1945), 67, 735-8, abstract only.*
JP 11228515, Machine English Translation, Feb. 11, 2008, Detailed Description Only, pp. 1-6.*
Patent Abstracts of Japan, vol. 2000, No. 01, Jan. 31, 2000, & JP 11 292855 A (Ube Ind. Ltd., Oct. 26, 1999.
Hennequin et al. (2002) "Novel 4-anilinoquinazolines with C-7 basic side chains. Design and structure activity relationship of a series of potent, orally active, VEGF receptor tyrosine kinase inhibitors" J. Med. Chem. 45: 1300-1312.

* cited by examiner

*Primary Examiner*—Rebecca L Anderson
(74) *Attorney, Agent, or Firm*—Morgan Lewis & Bockius LLP

(57) ABSTRACT

Chemical processes and intermediates useful in the manufacture of the quinazoline derivative 4-(3'-chloro-4'-fluoroanilino)-7-methoxy-6-(3-morpholinopropoxy)quinazoline, in particular processes for the manufacture of 7-methoxy-6-(3-morpholinopropoxy)-3,4-dihydroquinazolin-4-one of Formula II

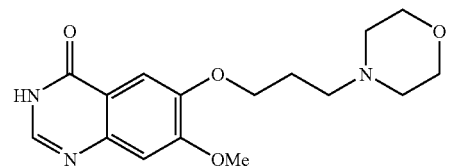

and 4-methoxy-5-(3-morpholinopropoxy)-2-nitrobenzonitrile of Formula III

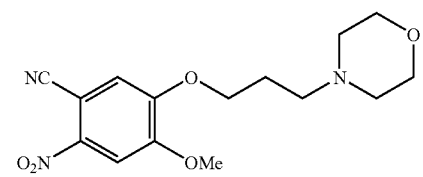

and their use in the manufacture of the quinazoline derivative.

2 Claims, No Drawings

PROCESS FOR THE PREPARATION OF 4-(3'-CHLORO-4'-FLUOROANILINO)-7-METHOXY-6-(3-MORPHOLINOPROPOXY) QUINAZOLINE

CROSS-REFERENCE TO RELATED APPLICATIONS

The present application is a U.S. National Phase Application of International Application No. PCT/GB2003/003923 (filed Sep. 9, 2003) which claims the benefit of Great Britain Patent Application No. 0221245.4 (filed Sep. 13, 2002).

The present invention relates to improved chemical processes and intermediates useful in the manufacture of compounds that possess antiproliferative properties and are useful in the treatment or prevention of cancers in a warm-blooded animal such as man. In particular, the present invention relates to chemical processes and intermediates useful in the manufacture of quinazoline derivatives, or pharmaceutically-acceptable salts thereof, which possess anti-proliferative activity. The invention also relates to processes for the manufacture of said intermediates and to processes for the manufacture of such quinazoline derivatives utilising said intermediates.

In particular, the present invention relates to chemical processes and intermediates useful in the manufacture of the quinazoline derivative 4-(3'-chloro-4'-fluoroanilino)-7-methoxy-6-(3-morpholinopropoxy)quinazoline which compound is disclosed in Example 1 of International Patent Application WO 96/33980. That compound is an inhibitor of the epidermal growth factor receptor (EGFR) family of tyrosine kinase enzymes such as erbB1 and possesses anti-proliferative activity such as anti-cancer activity and, accordingly, is useful in methods of treatment of proliferative disease such as cancer in the human or animal body.

That compound has the structure of Formula I

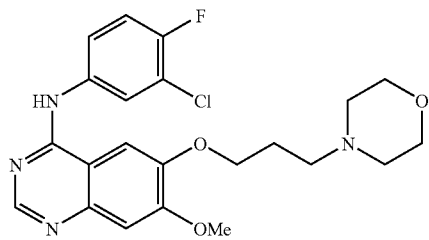

and is now known as Iressa (registered trade mark) and gefitinib (Unites States Adopted Name) and by way of the code number ZD1839 and Chemical Abstracts Registry Number 184475-35-2.

Two routes for preparing the compound of Formula I are disclosed in International Patent Application WO 96/33980. Each route involves the use of the compound 4-(3'-chloro-4'-fluoroanilino)-6-hydroxy-7-methoxyquinazoline as an intermediate with the formation of the 3-morpholinopropoxy side-chain at the 6-position occurring at the end of the synthesis. These existing routes are satisfactory for the synthesis of relatively small amounts of the compound of Formula I but they involve linear rather than convergent syntheses, each requiring the multiple use of chromatographic purification steps and the isolation of a substantial number of intermediates. As such, the overall yields of these syntheses are not high. There is therefore a need for a more efficient synthesis of the compound of Formula I suitable for use to make larger quantities of that compound. The new synthesis should not involve costly and time-consuming chromatographic purification procedures.

We have now devised a suitable process for the manufacture of the compound of Formula I. The new process is advantageous in that it allows the final product to be made in high quality and yield on a large scale. The process is more convergent than the previous routes and allows a substantial reduction in the number of intermediates that must be isolated. This provides significant advantages of time and cost. Chromatographic purification procedures are not required. According to the invention, processes are provided for the manufacture of key intermediates that may be used in the preparation of the compound of Formula I.

According to a first aspect of the present invention, there is provided a process for the manufacture of 7-methoxy-6-(3-morpholinopropoxy)-3,4-dihydroquinazolin-4-one of Formula II

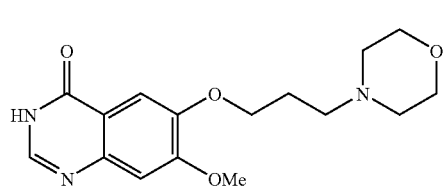

which comprises:—
(a) the reduction of 4-methoxy-5-(3-morpholinopropoxy)-2-nitrobenzonitrile of Formula III

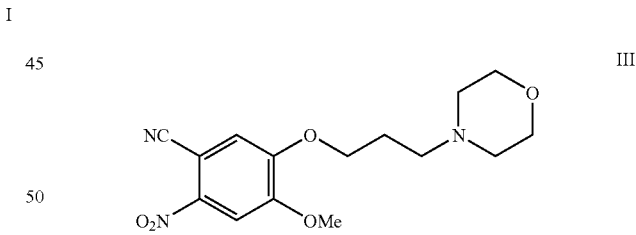

to give 2-amino-4-methoxy-5-(3-morpholinopropoxy)benzonitrile of Formula IV

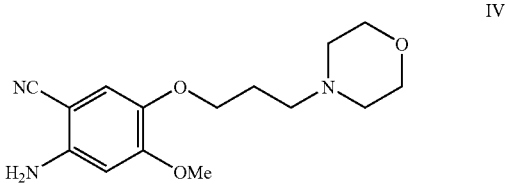

(b) the hydration of the compound of Formula IV to give 2-amino-4-methoxy-5-(3-morpholinopropoxy)benzamide of Formula V

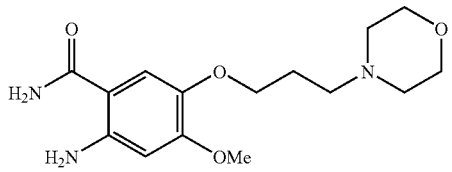

and (c) the cyclisation reaction of the compound of Formula V with formic acid, or a reactive derivative thereof, to give the compound of Formula II.

For process step (a), the reduction may conveniently be carried out by any of the many procedures known for such a transformation. The reduction may be carried out, for example, by the hydrogenation of a solution of the nitro compound in the presence of a suitable metal catalyst such as palladium or platinum on an inert carrier such as carbon and/or barium sulphate and in an inert solvent or diluent such as water, a polar protic solvent such as methanol or ethanol or a polar aprotic solvent such as ethyl acetate. A further suitable reducing agent is, for example, an activated metal such as activated iron (produced by washing iron powder with a dilute solution of an acid such as hydrochloric, hydrobromic, sulphuric or acetic acid). Thus, for example, the reduction may be carried out by heating a mixture of the nitro compound and the activated metal in a suitable solvent or diluent such as a polar protic solvent or a mixture of water and an alcohol, for example methanol or ethanol, at a temperature in the range, for example, 30 to 150° C., conveniently at or near 70° C. Further suitable reaction conditions include, for example, the use of ammonium formate or hydrogen gas in the presence of a catalyst, for example a metallic catalyst such as palladium-on-carbon. Conveniently, the reduction is carried out in the presence of a water-soluble inorganic reducing agent such as sodium dithionite and at a temperature in the range, for example, 20 to 100° C., conveniently at or near 50° C.

For process step (b), the reaction may conveniently be carried out by any of the many procedures known for such a transformation. The hydration may be carried out, for example, by reaction under acidic or basic conditions. A suitable base is, for example, an alkali metal, alkaline earth metal or ammonium carbonate or hydroxide, for example sodium carbonate, potassium carbonate, sodium hydroxide, potassium hydroxide or ammonium hydroxide. The reaction may conveniently be carried out in the presence of water and a suitable solvent or diluent such as a polar protic solvent such as methanol, ethanol, propanol, butanol or pentanol. The reaction may be carried out at a temperature in the range 20 to 150° C., suitably at or near 75° C. Conveniently, the hydration reaction is carried out in the presence of an alkali metal base such as potassium hydroxide, in a polar protic solvent such as 2-butanol, tert-butanol or tert-amyl alcohol and at a temperature in the range, for example, 60 to 100° C., conveniently at or near 80° C.

For process step (c), a suitable reactive derivative of formic acid is, for example, a formic acid amide such as formamide or N,N-dimethylformamide; a mixed anhydride, for example an anhydride formed by the reaction of formic acid and a chloroformate such as isobutyl chloroformate; the product of the reaction of formic-acid with a carbodiimide such as dicyclohexylcarbodiimide or 1-(3-dimethylaminopropyl)-3-ethylcarbodiimide; or the product of the reaction of formic acid with a mixture of an azo compound such as diethyl or di-tert-butyl azodicarboxylate and a phosphine such as triphenylphosphine.

The cyclisation reaction may conveniently be carried out in the presence of a suitable inert solvent or diluent, for example a polar aprotic solvent such as acetonitrile, ethyl acetate, tetrahydrofuran or 1,4-dioxan or a dipolar aprotic solvent such as N,N-dimethylformamide, N,N-dimethylacetamide, N-methylpyrrolidin-2-one or dimethylsulphoxide. Conveniently, the reaction may be carried out in the presence of an excess of formamide which acts as a reactant and as a solvent. The reaction is conveniently carried out at a temperature in the range, for example, 50 to 150° C., conveniently at or near 100° C. Conveniently, the cyclisation reaction is carried out in the presence of formic acid and formamide and at a temperature in the range, for example, 50 to 150° C., conveniently at or near 100° C.

The intermediate of Formula IV is a novel compound that forms a further feature of the present invention. Conveniently, the intermediates of Formula IV and V are not isolated as such but are each prepared and used as a solution in an organic solvent. Thereby, the compound of Formula II may be manufactured from the compound of Formula III in a one-pot procedure.

This first aspect of the present invention provides the compound of Formula II in commercially acceptable yields and of high quality. The preparation of the compound of Formula II was previously described in International Patent Application WO 01/04102 within Example 25, the synthetic route involving cleavage of the compound of Formula I under acidic conditions at elevated temperature. The compound of Formula II has been given Chemical Abstracts Registry Number 199327-61-2. The compound of Formula V is also a known compound. It is described in Japanese Patent Application No. 11292855 within Reference Example 3 wherein it is stated that the compound may be synthesised from the corresponding 4,5-disubstituted anthranilic acid. The compound of Formula V has been given Chemical Abstracts Registry Number 246512-44-7.

Processes for the preparation of quinazolin-4-ones are described in Patent Applications WO 03/051849 (published 26 Jun. 2003) and WO 03/064377 (published 7 Aug. 2003) that involve the cyclisation of 2-aminobenzoic acid derivatives, for example using ammonia and formic acid or a derivative thereof such as a formic acid ester or an orthoformic acid ester.

The compound of Formula II may be converted into the compound of Formula I using conventional procedures. For example, the compound of Formula II may be reacted with a halogenating agent such as thionyl chloride, phosphorus oxychloride or a mixture of carbon tetrachloride and triphenylphosphine to provide 4-chloro-7-methoxy-6-(3-morpholinopropoxy)quinazoline of Formula VI

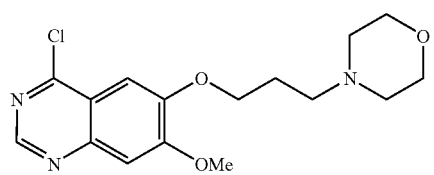

which may be reacted with 3-chloro-4-fluoroaniline in a displacement reaction to provide the compound of Formula I.

The displacement reaction may conveniently be carried out in the presence of a suitable acid or in the presence of a suitable base. A suitable acid is, for example, an inorganic acid such as, for example, hydrogen chloride or hydrogen bromide. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal hydride, for example sodium hydride. The reaction is conveniently carried out in the presence of a suitable inert solvent or diluent, for example an alcohol such as isopropanol, sec-butanol or tert-butanol, an ester such as ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 250° C., suitably in the range 40 to 120° C.

Typically, the displacement reaction may be carried out in the presence of a protic solvent such as isopropanol and at a temperature in the range, for example, 25 to 150° C., conveniently at or near the reflux temperature of the reaction solvent. Optionally, the displacement reaction may be carried out in the presence of an acid, for example hydrogen chloride gas in diethyl ether or the hydrogen chloride formed when the compound of Formula II is reacted with a halogenating agent such as thionyl chloride.

The compound of Formula I may be obtained from this process in the form of the free base or alternatively it may be obtained in the form of an acid addition salt such as a hydrochloride salt. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Conveniently, the intermediate of Formula VI is not isolated as such but is used as a solution or slurry in an organic solvent. Thereby, the compound of Formula I may be manufactured from the compound of Formula E in a one-pot procedure. An illustration of the conversion of the compound of Formula II into the compound of Formula I is provided hereinafter within Examples 2 to 4.

The procedures described in Examples 3 and 4 hereinafter concern the formation of a mono-solvate with dimethyl sulphoxide of the compound of Formula I and its conversion back to the compound of Formula I. These steps constitute a purification procedure that provides the compound of Formula I of greater purity and in a higher overall yield.

Each of the compounds of Formula II and Formula III and the intermediates of Formula IV and Formula V are useful in processes for the manufacture of pharmacologically effective quinazoline derivatives such as the compound of Formula I.

The 2-nitrobenzonitrile compound of Formula III is a novel compound that forms the starting material for the process that results in the manufacture of the compound of Formula II. As such the compound of Formula III is a novel chemical intermediate that forms a further feature of the present invention.

A process for the production of mono nitrated aromatic ether compounds is described in International Patent Application WO 02/48089 (published on 20 Jun. 2002). It is disclosed therein that, for example, a 4-alkoxybenzoic acid ester may be mono-nitrated by reaction with 1 to 2 equivalents of nitric acid in the presence of sulphuric acid and an organic solvent. There is the disclosure of the compound methyl 4-methoxy-5-(3-morpholinopropoxy)-2-nitrobenzoate (Examples 5 and 6 thereof) but the 2-nitrobenzonitrile compound of Formula III is not disclosed.

According to a second aspect of the present invention, there is provided a process for the manufacture of 4-methoxy-5-(3-morpholinopropoxy)-2-nitrobenzonitrile of Formula III

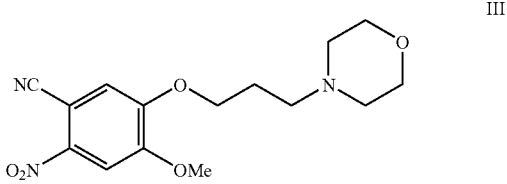

III which comprises:—
(a) the coupling of 3-hydroxy-4-methoxybenzonitrile of Formula VII

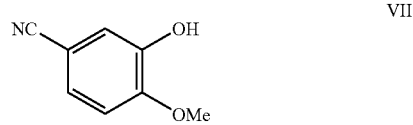

VII with a 3-morpholinopropane derivative of Formula VIII

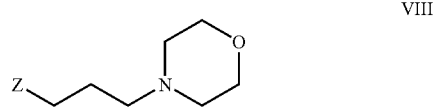

VIII wherein Z is a displaceable group to give 4-methoxy-3-(3-morpholinopropoxy)benzonitrile of Formula IX

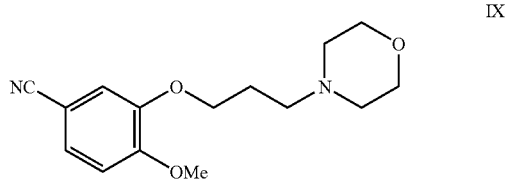

IX and (b) the nitration of the compound of Formula IX to give 4-methoxy-5-(3-morpholinopropoxy)-2-nitrobenzonitrile of Formula III.

For process step (a), the coupling step may conveniently be an alkylation reaction which may be carried out by any of the many procedures known for such a transformation. For an alkylation reaction, a suitable displaceable group Z is, for example, a halogeno, alkoxy, aryloxy or sulphonyloxy group, for example a chloro, bromo, methoxy, phenoxy, methanesulphonyloxy or 4-toluenesulphonyloxy group. The alkylation may be carried out, for example, in the presence of a suitable base and in a suitable inert solvent or diluent and at a temperature in the range, for example, 10 to 150° C., conveniently at or near 80° C.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal hydride, for example sodium hydride.

A suitable inert solvent or diluent, for example an alcohol such as methanol, ethanol or isopropanol, a halogenated solvent such as methylene chloride, chloroform or carbon tetrachloride, an aromatic solvent such as toluene, a polar aprotic solvent such as acetonitrile, ethyl acetate, tetrahydrofuran or 1,4-dioxan or a dipolar aprotic solvent such as N,N-dimethylformamide, N,N-dimethylacetamide, N-methylpyrrolidin-2-one or dimethylsulphoxide.

Alternatively, for process step (a), the coupling step may conveniently be a dehydration reaction which may be carried out in the presence of a suitable dehydrating agent. For a dehydration reaction, a suitable displaceable group Z is, for example, a hydroxy group. A suitable dehydrating agent is, for example, a carbodiimide reagent such as dicyclohexylcarbodiimide or 1-(3-dimethylaminopropyl)-3-ethylcarbodiimide or a mixture of an azo compound such as diethyl or di-tert-butyl azodicarboxylate and a phosphine such as triphenylphosphine. The dehydration reaction is conveniently carried out in the presence of a suitable inert solvent or diluent, for example a halogenated solvent such as methylene chloride, chloroform or carbon tetrachloride and at a temperature in the range, for example, 10 to 150° C., conveniently at or near ambient temperature.

Conveniently, the coupling reaction is carried out as an alkylation reaction in the presence of an alkali metal carbonate such as potassium carbonate, in a dipolar aprotic solvent such as N,N-dimethylformamide and at a temperature in the range, for example, 40 to 120° C., conveniently at or near 80° C.

For process step (b), the nitration step may conveniently be carried out by any of the many procedures known for such a transformation. Conveniently, the nitration may be carried out using concentrated nitric acid, optionally in the presence of concentrated sulphuric acid and optionally in the presence of a polar protic solvent such as acetic acid, at a temperature in the range, for example, 0 to 80° C., conveniently at or near ambient temperature. Conveniently, the sulphuric acid concentration is greater than 50% (weight/weight % with water), preferably about 70%. On completion of the reaction, the reaction mixture is neutralised with an aqueous base such as sodium or ammonium hydroxide solution and the compound of Formula III is extracted into an organic solvent.

The intermediate of Formula IX is a novel compound that forms a further feature of the present invention. Moreover, the intermediate of Formula IX is useful in processes for the manufacture of pharmacologically effective quinazoline derivatives such as the compound of Formula I. Conveniently, the intermediate of Formula IX is not isolated as such but is prepared and used as a solution in an organic solvent. Thereby, the compound of Formula III may be manufactured from the compound of Formula VII in a one-pot procedure.

This second aspect of the present invention provides the compound of Formula III in commercially acceptable yields and of high quality.

The processes of the invention provide significantly improved yields and quality of intermediates than those previously used in the manufacture of the compound of Formula I. Conveniently, the compound of Formula VII may be converted into the compound of Formula III in a one pot procedure, which compound may be converted into the compound of Formula II in a second one pot procedure, which compound may be converted, in turn, into the compound of Formula I in a third one pot procedure. Thus the compound of Formula I may be manufactured with the prior isolation of just two intermediates.

The invention is further illustrated, but not limited, by the following Examples.

EXAMPLE 1

Preparation of 7-methoxy-6-3-morpholinopropoxy)-3,4-dihydroquinazolin-4-one

Sodium dithionite (89%, 81.4 kg) was added to a stirred slurry of 4-methoxy-5-(3-morpholinopropoxy)-2-nitrobenzonitrile (48.8 kg) in water (867 liters) and the resultant mixture was heated to 50° C. for approximately 2 hours to complete the reaction. The temperature of the reaction mixture was raised to approximately 70° C. and a concentrated aqueous hydrochloric acid solution (36%, 270 kg) was added over 3 hours. The resultant mixture was cooled to 20-25° C. and sodium hydroxide liquor (47%, 303.7 kg) was added whilst stirring of the reaction mixture was continued. The reaction mixture was extracted with two portions of methylene chloride (1082 kg and 541 kg respectively) and the combined organic extracts were washed with water (510 liters). The organic phase was concentrated by distillation to remove 800 liters of solvent. There was thus obtained a methylene chloride solution (503.5 kg) containing 2-amino-4-methoxy-5-(3-morpholinopropoxy)benzonitrile (46.3 kg, 99% yield) suitable for use in the next stage.

[A portion of the 2-amino-4-methoxy-5-(3-morpholinopropoxy)benzonitrile was isolated using the following procedure:—

A sample of the methylene chloride solution was evaporated. There was thus obtained 2-amino-4-methoxy-5-(3-morpholinopropoxy)benzonitrile as a solid, m.p. 87.5° C.; NMR Spectrum: (DMSOd$_6$) 1.79 (m, 2H), 2.36 (t, 4H), 2.36 (t, 2H), 3.56 (t, 4H), 3.73 (s, 3H), 3.86 (t, 2H), 5.66 (br s, 2H), 6.4 (s, 1H), 6.89 (s, 1H; Mass Spectrum: M+H$^+$ 292.]

After repetition of the reduction step, a methylene chloride solution (894.3 kg) containing 2-amino-4-methoxy-5-(3-morpholinopropoxy)benzonitrile (81.6 kg) was added portionwise to tert-amyl alcohol (186 kg) and the resultant mixture was distilled until the temperature of the distillate reached 57° C. Additional tert-amyl alcohol (726 kg) was added portionwise and distillation was continued until the residual volume of the reaction mixture was approximately 770 liters. Potassium hydroxide (flaked form; 51 kg) was added and the mixture was heated to 79° C. for 4 hours. The resultant mixture was cooled to ambient temperature to provide a solution of 2-amino-4-methoxy-5-(3-morpholinopropoxy)benzamide which was used without being isolated.

[A portion of the 2-amino-4-methoxy-5-(3-morpholinopropoxy)benzamide was isolated using the following procedure:—

A sample of the tert-amyl alcohol solution was evaporated to give an oil. Methylene dichloride and water were added and the mixture was heated to reflux. The resultant mixture was allowed to cool to ambient temperature. The precipitated solid was isolated. The filtrate was dried over magnesium sulphate and evaporated to give an oil. The precipitated solid and the oil were combined, dissolved in hot ethyl acetate and washed with water. The warm organic solution was separated and isohexane was added to initiate crystallisation. The resultant mixture was cooled to ambient temperature and the precipitate was isolated, washed with cold ethyl acetate and dried. There was thus obtained 2-amino-4-methoxy-5-(3-morpholinopropoxy)benzamide as a solid, m.p. 153.5° C.; NMR Spectrum: (DMSOd$_6$) 1.8 (m, 2H), 2.4 (t, 4H), 2.4 (t, 2H), 3.56 (t, 4H), 3.7 (s, 3H), 3.88 (t, 2H), 6.27 (s, 1H), 6.43 (br s, 2H), 6.81 (br s, 1H), 7.13 (s, 1H), 7.56 (br s, 1H); Mass Spectrum: M+H$^+$ 310.]

The solution so obtained was acidified with formic acid (45.8 kg) and the resultant mixture was concentrated by distillation under reduced pressure (0.12 bar) to remove 460 liters of solvent. Formamide (438 kg) was added and distillation at reduced pressure (0.12 bar) was continued until the distillation temperature reached 95° C. The mixture was heated for a further 5 hours at approximately 100° C. The mixture was cooled to 20° C. and the resulting solid was collected by filtration, washed in turn with water, isopropanol and tert-butyl methyl ether and dried. There was thus obtained 7-methoxy-6-(3-morpholinopropoxy)-3,4-dihydro-quinazolinone (63 kg); NMR Spectrum: (DMSOd$_6$) 1.93 (m, 2H), 2.37 (t, 4H), 2.43 (t, 2H), 3.58 (t, 4H), 3.91 (s, 3H), 4.11 (t, 2H), 7.13 (s, 1H), 7.44 (s, 1H), 7.98 (s, 1H), 12.05 (broad s, 1H); Mass Spectrum: M+H$^+$ 320.

EXAMPLE 2

Preparation of 4-(3'-chloro-4'-fluoroanilino)-7-methoxy-6-(3-morpholinopropoxy)quinazoline Whilst maintaining the temperature of the reaction mixture at about 50° C., phosphorus oxychloride (365 kg) was added to a stirred slurry of 7-methoxy-6-(3-morpholinopropoxy)-3,4-dihydroquinazolin-4-one (220 kg), triethylamine (105 kg) and toluene (1790 liters). The resultant mixture was stirred at about 50° C. for 5 hours to complete the formation of 4-chloro-7-methoxy-6-(3-morpholinopropoxy)quinazoline.

The resultant stirred slurry was cooled to about 0° C. and isopropanol (527 liters) was added whilst the temperature of the reaction mixture was maintained between 0° and 5° C. The reaction mass was warmed to about 20° C. and held at that temperature for about 1 hour. A solution of 3-chloro-4-fluoroaniline (168 kg) in isopropanol (228 liters) was added and the resultant reaction mixture was stirred and warmed to about 66° C. and held at that temperature for about 1 hour. The mixture was stirred and cooled to about 30° C. and isopropanol (662 liters) and water (1486 liters) were added in turn. A mixture of aqueous sodium hydroxide liquor (47% w/w, 755 kg) and water (40 liters) was added portionwise to the stirred reaction mixture. The resultant mixture was warmed to about 64° C. and the two liquid phases were allowed to separate. The lower aqueous layer was run off. The remaining organic phase was initially cooled to about 30° C., warmed to about 50° C. and finally cooled to about 20° C. at a rate of about 10° C. per hour. The resultant solid was collected by filtration, washed in turn with isopropanol and ethyl acetate and dried with warm nitrogen gas (60° C.). There was thus obtained 4-(3'-chloro-4'-fluoroanilino)-7-methoxy-6-(3-morpholinopropoxy)quinazoline (224 kg), m.p. about 194° C. to 198° C.

EXAMPLE 3

Preparation of 4-(3'-chloro-4'-fluoroanilino)-7-methoxy-6-(3-morpholinopropoxy)quinazoline mono-solvate with dimethyl sulphoxide With warming to about 75° C., 4-(3'-chloro-4'-fluoroanilino)-7-methoxy-6-(3-morpholinopropoxy)quinazoline (204 kg) was dissolved in a mixture of ethyl acetate (1021 liters) and dimethyl sulphoxide (181 liters) containing diatomaceous earth filter aid (5 kg). The resultant mixture was filtered and ethyl acetate (78 liters) was used to wash the filter aid solid. The filtrate and washings were combined and cooled initially to about 10° C. The mixture was then heated to about 40° C. for 1 hour. The warm mixture was cooled to 0° C. at a rate of about 10° C. per hour. The resultant solid was collected by filtration. There was thus obtained the title compound as a mono-solvate with dimethyl sulphoxide, m.p. about 194° C. to 198° C. occurring after an endotherm at approximately 130° C. relating to a DMSO desolvation point in the range of about 125° C. to 135° C.

EXAMPLE 4

Desolvation of 4-(3'-chloro-4'-fluoroanilino)-7-methoxy-6-(3-morpholinopropoxy)quinazoline mono-solvate with dimethyl sulphoxide 4-(3'-Chloro-4'-fluoroanilino)-7-methoxy-6-(3-morpholinopropoxy)quinazoline mono-solvate with dimethyl sulphoxide (from Example 3) was washed with ethyl acetate (581 liters). The washed solid was mixed with ethyl acetate (895 liters) and the resultant slurry was stirred and heated to 34° C. for about 1 hour. The mixture was then cooled to 0° C. and held at that temperature for 2 hours to allow crystallisation to proceed. The resultant solid was separated by filtration, washed with ethyl acetate (580 liters) and dried in a flow of warm nitrogen gas (60° C.). There was thus obtained 4-(3'-chloro-4'-fluoroanilino)-7-methoxy-6-(3-morpholinopropoxy)quinazoline (161 kg), m.p. about 194° C. to 198° C.

EXAMPLE 5

Preparation of 4-methoxy-5-(3-morpholinopropoxy)-2-nitrobenzonitrile

A mixture of 3-hydroxy-4-methoxybenzonitrile (34.3 kg), potassium carbonate (54.5 kg) and N,N-dimethylformamide (226 kg) was stirred and heated to approximately 85° C. A toluene solution (91.4 kg) containing N-(3-chloropropyl)morpholine (41.1 kg) was added to the heated mixture and the resultant mixture was heated to about 85° C. for an additional 10 hours. The bulk of the N,N-dimethylformamide was removed by vacuum distillation and the residue was diluted with water (286 liters). The aqueous mixture was extracted with three portions of a 1:1 mixture of heptane and ethyl acetate (239 liters, 139 liters and 139 liters respectively). The combined organic layers were washed with water, concentrated to approximately 150 liters by vacuum distillation and diluted with glacial acetic acid (133 kg). Additional solvent was removed by vacuum distillation. Addition of glacial acetic acid (84 kg) provided a solution of 4-methoxy-3-(3-morpholinopropoxy)benzonitrile (62.5 kg) in acetic acid (122 kg) which was used without further purification.

[A portion of the 4-methoxy-3-(3-morpholinopropoxy) benzonitrile was isolated using the following procedure:—

A sample of the heptane and ethyl acetate solution was washed with water and evaporated to leave an oil. The oil was partitioned between tert-butyl methyl ether and water. The organic solution was dried over magnesium sulphate and evaporated. The residue was triturated under heptane and the resultant solid was isolated and dried at ambient temperature. There was thus obtained 4-methoxy-3-(3-morpholinopropoxy)benzonitrile, m.p. 52.4° C.; NMR Spectrum: (DMSOd$_6$) 1.87 (m, 2H), 2.38 (t, 4H), 2.38 (t, 2H), 3.57 (t, 4H), 3.84 (s, 3H), 4.05 (t, 2H), 7.11 (d, 1H), 7.39 (s, 1H), 7.42 (s, 1H); Mass Spectrum: M+H$^+$ 277.]

Whilst the temperature of the reaction mixture was cooled to less than or equal to 20° C., a solution of 4-methoxy-3-(3-morpholinopropoxy)benzonitrile (62.5 kg) in acetic acid (122 kg) was added to a stirred mixture of sulphuric acid (70%, 245 kg) and nitric acid (70%, 31 kg). After 2 hours, additional nitric acid (3.4 kg) was added and the resultant mixture was stirred as approximately 20° C. for 50 hours. The mixture so obtained was added to water (1115 liters) and the resultant mixture was warmed to 30-35° C. The mixture was basified to about pH11 by the addition of concentrated sodium hydroxide liquor. The reaction mixture was extracted with three portions of methylene chloride (679 kg, 272 kg and 272 kg respectively) and the combined organic extracts were filtered to remove particulate matter. The methylene chloride was removed by a sequence of distillation/addition steps involving the addition of six equal portions of ethyl acetate (total 840 liters). There was thus obtained a warmed (65° C.) solution of the reaction product in ethyl acetate (360 liters). The solution was cooled to 5° C. and the precipitate was isolated by filtration. There was thus obtained 4-methoxy-5-(3-morpholinopropoxy)-2-nitrobenzontrile (56.4 kg), m.p. 127° C.; NMR Spectrum: (DMSOd$_6$) 1.92 (m, 2H), 2.36 (m, 4H), 2.41 (t, 2H), 3.58 (m, 4H), 3.98 (s, 3H), 4.24 (t, 2H), 7.69 (s, 1H), 7.86 (s, 1H); Mass Spectrum: M+H$^+$ 322.

The 3-hydroxy-4-methoxybenzonitrile solution used as a starting material was obtained as follows:—

3-Hydroxy-4-methoxybenzaldehyde (36.7 kg) and sodium formate (30.6 kg) were added to formic acid (96%, 204 kg) and the resultant mixture was heated to approximately 85° C. Hydroxylamine sulphate (21.6 kg) was added in eight equal portions at 30 minute intervals and the mixture was heated to 85° C. for 5 hours. The resultant mixture was cooled to approximately 25° C. and added to a solution of sodium chloride (140 kg) in water (700 liters). The resultant solid was collected by filtration, washed with water and dried to give 3-hydroxy-4-methoxybenzonitrile (34 kg, 94%; Chemical Abstracts Registry Number 5280546-6).

The N-(3-chloropropyl)morpholine solution used as a starting material was obtained as follows:—

A mixture of morpholine (178.5 kg) and toluene (560 liters) was stirred and warmed to approximately 77° C. 1-Bromo-3-chloropropane (147 kg) was added slowly over approximately 2 hours and the resultant mixture was heated at approximately 77° C. for a further 20 hours. The mixture was cooled to ambient temperature and diluted with additional toluene (293 liters). The mixture was extracted with dilute aqueous hydrochloric acid solution (18%, 206 kg). The aqueous layer was separated, basified to pH9-10 by the addition of concentrated aqueous sodium hydroxide solution and extracted with toluene (250 liters). The resultant toluene layer was concentrated by distillation until a distillate having b.p. 56° C. at 0.065 bar was obtained. There was thus obtained a toluene solution (129 kg) containing N-(3-chloropropyl)morpholine (58 kg; Chemical Abstracts Registry Number 7357-67-7) that was used without further purification.

The invention claimed is:

1. A process for the manufacture of 7-methoxy-6-(3-morpholinopropoxy)-3,4-dihydroquinazolin-4-one of Formula II

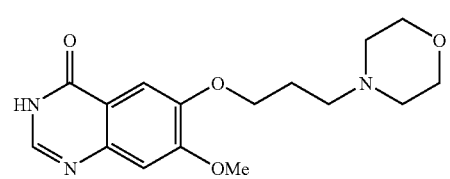

which comprises:

(a) the reduction of 4-methoxy-5-(3-morpholinopropoxy)-2-nitrobenzonitrile of Formula III

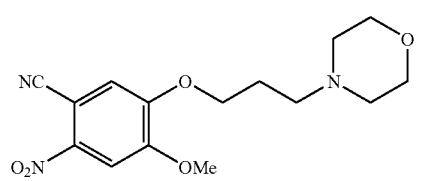

to give 2-amino-4-methoxy-5-(3-morpholinopropoxy) benzonitrile or Formula IV

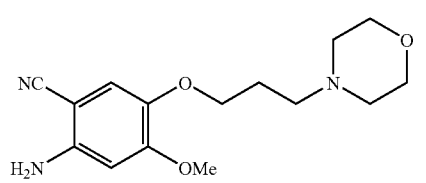

wherein an aqueous slurry of the compound of Formula III is heated in the presence of a water-soluble inorganic reducing agent and the compound of Formula IV so formed is not isolated as such but is extracted as an organic phase with an organic solvent, which organic phase is added to a polar protic solvent and extracting organic solvent is removed by distillation and the resultant solution comprising the intermediate of Formula IV in said polar protic solvent is subjected to the hydration of step (b);

(b) the hydration of the compound of Formula IV to give 2-amino-4-methoxy-5-(3-morpholinopropoxy)benzamide of Formula V

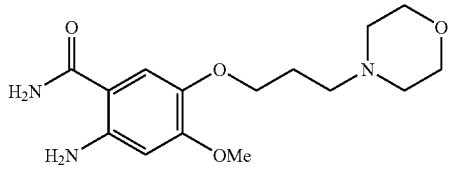

wherein the reaction is carried out in the resultant solution from step (a) in the presence of an alkali metal base and in a polar protic solvent to form a reaction mixture comprising the compound of Formula V, and wherein the compound of Formula V so formed is not isolated from the reaction mixture as such but is prepared and used in the cyclisation reaction of step (c) as a solution in said polar protic solvent; and (c) the cyclisation reaction of the compound of Formula V to give the compound of Formula II wherein the reaction mixture from step (b) is acidified with formic acid, the resultant mixture is concentrated by distillation under reduced pressure and an excess of formamide is added to act as a reactant and as a solvent, the resultant solution is maintained at an elevated temperature to form compound of Formula II, whereafter the solution is cooled whereby compound of Formula II comes out of solution as a solid precipitate and optionally is removed from the cooled solution by filtration.

2. A process for the manufacture of 7-methoxy-6-(3-morpholinopropoxy)-3,4-dihydroquinazolin-4-one of Formula II

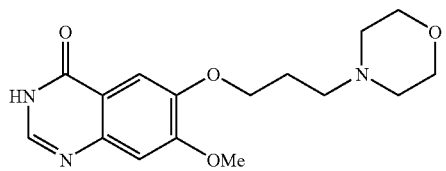

which comprises:
(a) the reduction of 4-methoxy-5-(3-morpholinopropoxy)-2-nitrobenzonitrile of Formula III

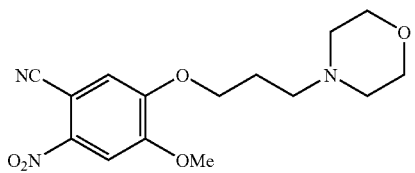

to give 2-amino-4-methoxy-5-(3-morpholinopropoxy)benzonitrile of Formula IV

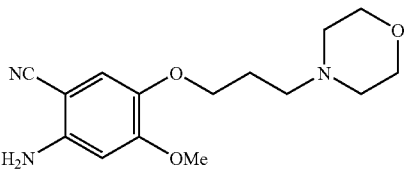

wherein an aqueous slurry of the compound of formula III is heated in the presence of the water-soluble inorganic reducing agent sodium dithionite and the compound of Formula IV so formed is not isolated as such but is extracted as an organic phase with methylene chloride, which organic phase is added to the polar protic solvent tert-amyl alcohol and methylene chloride is removed by distillation and the resultant solution comprising the intermediate of Formula IV in tert-amyl alcohol is subjected to the hydration of step (b);

(b) the hydration of the compound of Formula IV to give 2-amino-4-methoxy 5-(3)morpholinopropoxy)benzamide of Formula V

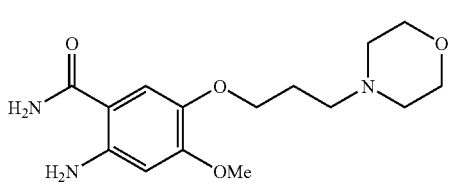

wherein the reaction is carried out in the resultant solution from step (a) in the presence of the alkali metal base potassium hydroxide and in the polar protic solvent tert-amyl alcohol and at a temperature at or near 80° C. to form a reaction mixture comprising the compound of Formula V, and wherein the compound of Formula V so formed is not isolated from the reaction mixture as such but is prepared and used in the cyclisation reaction of step (c) as a solution in tert-amyl alcohol; and (c) the cyclisation reaction of the compound of Formula V to give the compound of Formula II, wherein the reaction mixture from step (b) is acidified with formic acid, the resultant mixture is concentrated by distillation under reduced pressure, an excess of formamide is added to act as a reactant and as a solvent and the resultant solution is heated to a temperature at or near 100° C. to form compound of Formula II, whereafter the solution is cooled whereby compound of Formula II comes out of solution as a solid precipitate and optionally is removed from the cooled solution by filtration.

* * * * *